United States Patent [19]

Jorgensen

[11] Plant 4,105

[45] Sept. 13, 1977

[54] CHRYSANTHEMUM PLANT

[75] Inventor: Sigvart Jorgensen, Shelby, N.C.

[73] Assignee: Patterson's Flowers, Inc., Shelby, N.C.

[21] Appl. No.: 708,288

[22] Filed: July 23, 1976

[51] Int. Cl.[2] ..... A01H 5/00

[52] U.S. Cl. ..... Plt./76

[58] Field of Search ..... Plt./76, 80–81

*Primary Examiner*—Robert E. Bagwill

*Attorney, Agent, or Firm*—Donald D. Jeffery

[57] ABSTRACT

This invention relates to a mutation of Deep Snow Pink chrysanthemum, and differs therefrom by its purple florets.

2 Drawing Figures

The present invention comprises a new and distinct cultivar of *Chrysanthemum morifolium,* Ramat., hereinafter referred to by the cultivar name Snow Purple (No. 63924S01).

Snow Purple is a spontaneous sport of Deep Snow Pink (No. 63924B01; unpatented; commercially available). Snow Purple was discovered and selected by Sigvart Jorgensen in October, 1974 as one plant within a flowering block of Deep Snow Pink in a controlled environment in Shelby, N.C.

The first act of asexual reproduction of Snow Purple was accomplished when vegetative cuttings were taken from the initial selection in the late fall of 1974 in a controlled environment in Shelby, N.C. by Sigvart Jorgensen. Horticultural examination of selected units initiated Jan. 12, 1976 has demonstrated that the combination of characteristics as herein disclosed for Snow Purple are firmly fixed and are retained through successive generations of asexual reproduction.

Snow Purple has not been observed under all possible environmental conditions. The phenotype may vary significantly with variations in environment such as temperature, light intensity, and daylength. The following observations, measurements, and comparisons describe plants grown in Shelby, N.C. under greenhouse environmental conditions which approximate those generally used in commercial practice, as described in Chart A which appears at the end of this specification.

The following traits have been repeatedly observed and are determined to be basic characteristics of Snow Purple which in combination distinguish this chrysanthemum as a new and distinct cultivar;

1. Decorative inflorescence type.
2. Flat inflorescence form.
3. Purple inflorescence color with uniform color oxidation.
4. Diameter across face of inflorescence up to 9 cm. at maturity.
5. Uniform eight week flowering response to photoperiodic short-day control.
6. Short plant height (requiring two to three long day weeks prior to short days and one application of 2500 ppm B-9 SP 14 to 21 days after the beginning of short days to attain a flowered plant height of 30 to 45 cm).
7. Semi-spreading branching pattern.

The accompanying photographic drawing shows typical inflorescence and foliage characteristics of Snow Purple. It is noted that difficulty was encountered in obtaining a photograph accurately representing the true inflorescence color of Snow Purple. The color readings in the following description are, however, correct.

Of the many commercial cultivars known to the present inventors, the most similar existing cultivar in comparison to Snow Purple is Always Pink (No. 63924A01, the disclosure of which appears in U.S. Plant Pat. No. 3,256), which is also a sport of Deep Snow Pink. Reference is made to attached Chart B which compares certain characteristics of Snow Purple with the same characteristics of Always Pink. It will be noted that Snow Purple has a different (more purple) inflorescence color than Always Pink. The diameter across face of inflorescence, plant height, branching pattern, flowering response, inflorescence form, and inflorescence type of Snow Purple are similar to those same characteristics of Always Pink.

In the following description, color references are made to The Munsell Limit Color Cascade, 1972 edition. The color values were determined between 9:30 and 10:00 A.M. on Apr. 20, 1976 under 150 foot-candle light intensity at Barberton, Ohio.

Botanical classification: *Chrysanthemum morifolium,* Ramat., cv. Snow Purple.

INFLORESCENCE

Capitulum (See Sheet 1):
- *Form.*—Flat.
- *Type.*—Decorative.
- *Permanence.*—10 days.
- *Diameter across.*—65 to 90 mm.

Corolla of ray florets:
- *Persistence.*—Resists shatter.
- *Color (abaxial).*—Approximately 46-12 but more greyed.
- *Color (adaxial).*—Approximately 46-6 but more greyed.

Reproductive organs:
- *Androecium.*—Rare; present disc florets only; scant pollen.
- *Gynoecium.*—Present both ray and disc florets.

PLANT

General appearance: semi-spreading; short height.

Foliage (See Sheet 1):
- *Color (abaxial).*—Approximately 21-13 to 21-15 overlaid with grey.
- *Color (adaxial).*—Approximately 21-13 overlaid with grey.

CHART A

AVERAGE GREENHOUSE CHRYSANTHEMUM ENVIRONMENTS USED FOR SHELBY, NORTH CAROLINA

| SEASON | TEMPERATURES USED Night | Bright Day | Cloudy Day | LIGHTING USED | BLACK CLOTH USED | SUPP $CO_2$ |
|---|---|---|---|---|---|---|
| FALL | 65° F to 56° F | 65° F to 80° F | 60° F to 75° F | 2 to 4 weeks at 3 Hours Per Night of 7–10 f.c. | To Sept. 15 on - 5:30 PM Off - 7:30 AM | From Oct. 15 300 ppm |
| WINTER | 58° F to 62° F | 65° F to 70° F | 60° F to 65° F | 2 to 5 weeks at 5 hours Per Night of 7–10 f.c. | NONE | 300 ppm |
| SPRING | 58° F to 65° F | 65° F to 80° F | 60° F to 75° F | 2 to 4 weeks at 5 Hours Per Night of 7–10 f.c. | From Mar. 15 on - 5:30 PM Off - 7:30 AM | To Apr. 15 300 ppm |
| SUMMER | 62° F to 68° F | 70° F to 90° F | 65° F to 75° F | 1 to 2 weeks at 3 Hours Per Night of 7–10 f.c. | On - 6:00 PM Off - 8:00 AM | NONE |

CHART B

COMPARISON OF SNOW PURPLE AND ALWAYS PINK

| CULTIVAR | INFLORESCENCE COLOR | DIAMETER ACROSS FACE OF INFLORESCENCE | PLANT HEIGHT | BRANCHING PATTERN | FLOWERING RESPONSE | INFLORESCENCE FORM AND TYPE |
|---|---|---|---|---|---|---|
| Snow Purple | Purple | 65 to 90 mm | Short | Semi-spreading | 8 week | Flat decorative |
| Always Pink | Lavender Pink | 75 to 90 mm | Short | Semi-spreading | 8 week | Flat decorative |

COMPARISONS MADE OF PLANTS GROWN IN A GREENHOUSE IN SHELBY, NORTH CAROLINA UNDER ENVIRONMENTAL CONDITIONS AS DESCRIBED IN CHART A.

I claim:

1. A new and distinct cultivar of *Chrysanthemum morifolium,* Ramat. known by the cultivar name Snow Purple and particularly characterized as to uniqueness by the combined characteristics of decorative inflorescence type; flat inflorescence form; purple inflorescence color with uniform color oxidation; diameter across face of inflorescence up to 9 cm. at maturity; uniform eight week flowering response to photoperiodic short-day control; short plant height; and semi-spreading branching pattern.

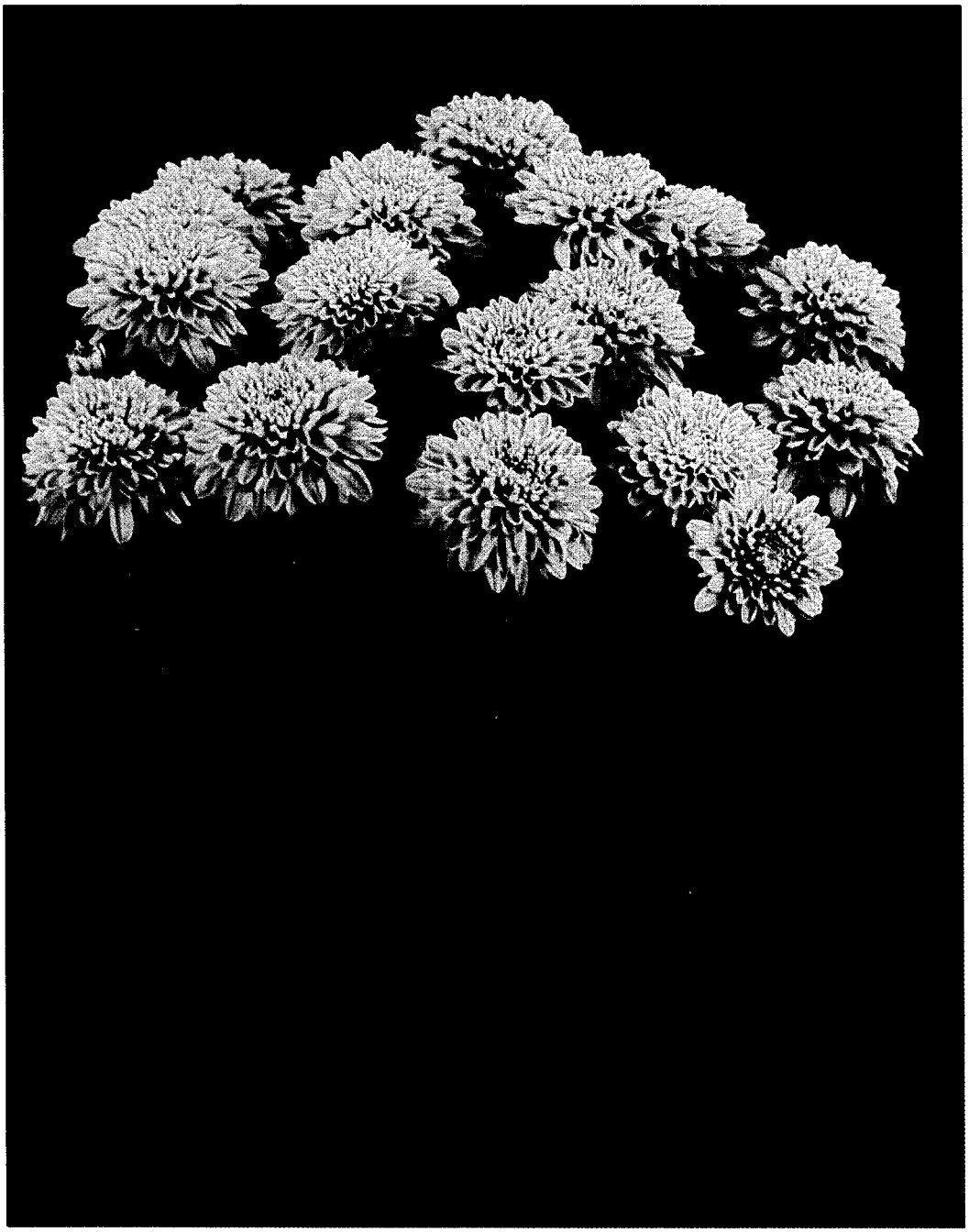

* * * * *